US012296071B2

(12) United States Patent
Pytel et al.

(10) Patent No.: US 12,296,071 B2
(45) Date of Patent: May 13, 2025

(54) FUNCTIONALISATION OF MEDICAL DEVICES

(71) Applicant: ConvaTec Technologies Inc., Las Vegas, NV (US)

(72) Inventors: Rachel Zimet Pytel, Newton, MA (US); Neal Robert Carty, Chicago, IL (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 0 days.

(21) Appl. No.: 17/564,673

(22) Filed: Dec. 29, 2021

(65) Prior Publication Data

US 2022/0202999 A1    Jun. 30, 2022

Related U.S. Application Data

(63) Continuation of application No. PCT/US2021/065471, filed on Dec. 29, 2021.

(60) Provisional application No. 63/132,213, filed on Dec. 30, 2020.

(51) Int. Cl.
| | |
|---|---|
| *A61L 29/08* | (2006.01) |
| *A61L 29/04* | (2006.01) |
| *B05D 1/00* | (2006.01) |
| *B05D 3/14* | (2006.01) |
| *B05D 5/02* | (2006.01) |

(52) U.S. Cl.
CPC .......... *A61L 29/085* (2013.01); *A61L 29/049* (2013.01); *B05D 1/62* (2013.01); *B05D 3/147* (2013.01); *B05D 3/148* (2013.01); *B05D 5/02* (2013.01); *A61L 2400/18* (2013.01); *A61L 2420/02* (2013.01); *B05D 2518/00* (2013.01)

(58) Field of Classification Search
CPC .............. B05D 1/62; B05D 1/18; H05H 1/46; C23C 18/285
See application file for complete search history.

(56) References Cited

U.S. PATENT DOCUMENTS

| | | | |
|---|---|---|---|
| 5,080,924 A | | 1/1992 | Kamel et al. |
| 6,033,582 A | * | 3/2000 | Lee ........................... C23F 4/00 216/37 |
| 6,358,557 B1 | * | 3/2002 | Wang ....................... B05D 1/18 427/302 |
| 2007/0059449 A1 | * | 3/2007 | Ryu ....................... C23C 18/285 427/535 |
| 2008/0118734 A1 | | 5/2008 | Goodwin et al. |
| 2009/0065485 A1 | * | 3/2009 | O'Neill .................... H05H 1/46 219/121.48 |
| 2010/0072642 A1 | | 3/2010 | Broad et al. |
| 2011/0060402 A1 | | 3/2011 | Kitching et al. |

FOREIGN PATENT DOCUMENTS

| | | | |
|---|---|---|---|
| JP | 2019189754 A | 10/2019 | |
| WO | WO99/32235 | * 7/1999 | ............... B05D 7/24 |
| WO | 2006062611 A1 | 6/2006 | |

OTHER PUBLICATIONS

International Search Report; International Searching Authority; International Application No. PCT/US2021/065471; Apr. 18, 2022; 3 pages.
Written Opinion of the International Searching Authority; International Searching Authority; International Application No. PCT/US2021/065471; Apr. 18, 2022; 9 pages.
Zanini et al. "Plasma-induced graft-polymerization of polyethylene glycol acrylate on polypropylene films: Chemical characterization and evaluation of the protein adsorption" Journal of Colloid and Interface Science, vol. 341 Issue 1 (Sep. 16, 2009): pp. 53-58.
Dong et al. "Antifouling ability of polyethylene glycol of different molecular weights grafted onto polyester surfaces by cold plasma" Polymer Bulletin, vol. 66 (Aug. 11, 2010): pp. 517-528.
Dong et al. "Plasma-Mediated Grafting of Poly(ethylene glycol) on Polyamide and Polyester Surfaces and Evaluation of Antifouling Ability of Modified Substrates" Langmuir, vol. 23 Issue 13 (May 15, 2007): pp. 7306-7313.
Second Chinese Office Action; China National Intellectual Property Administration; Chinese Application No. 202180088154.9; May 25, 2024; 16 pages.
Extended European Search Report; European Patent Office; European Application No. 21916400.1; Oct. 14, 2024; 28 pages.
Wei et al., Plasma-induced graft polymerization of poly(ethylene glycol) on poly(methyl methacrylate) surfaces for improving antistatic property, Journal of Applied Polymer Science, 2010, vol. 118, Issue 2, p. 943-949.
Pinto et al., Poly( dimethyl siloxane) surface modification by low pressure plasma to improve its characteristics towards biomedical applications, Colloids and Surfaces B: Biointerfaces, 81, 2010, p. 20-26.
Labey et al., Antibiotic-loaded polypropylene surgical meshes with suitable biological behaviour by plasma functionalization and polymerization, Biomaterials, 71, 2015, p. 132-144.

* cited by examiner

*Primary Examiner* — Dah-Wei D. Yuan
*Assistant Examiner* — Andrew J Bowman
(74) *Attorney, Agent, or Firm* — TAFT STETTINIUS HOLLISTER LLP; Ryan O. White; Derek B. Lavender

(57) ABSTRACT

Methods of modifying medical devices and medical devices are disclosed. One embodiment of a method of modifying a medical device includes functionalizing a surface of the medical device using cold plasma. One embodiment of a medical device is obtained by a method of modifying a device that includes functionalizing a surface of the medical device using cold plasma.

14 Claims, No Drawings

FUNCTIONALISATION OF MEDICAL DEVICES

CROSS-REFERENCE TO RELATED APPLICATION(S)

The present application claims priority to U.S. Provisional Patent Application No. 63/132,213 entitled "FUNCTIONALISATION OF MEDICAL DEVICES," which was filed on Dec. 30, 2020. The contents of that application are incorporated by reference herein in their entirety.

FIELD OF THE DISCLOSURE

The present disclosure relates to medical devices, and in particular, methods of modifying surfaces of medical devices.

BACKGROUND OF THE DISCLOSURE

Catheters are medical devices adapted for insertion into the body to treat diseases or disorders or perform surgical procedures. The material and configuration of catheters may vary depending on the intended use thereof. Some applications of catheters include cardiovascular, urological, gastrointestinal, neurovascular, and ophthalmic applications, among others.

In some cases, catheters are inserted into a cavity, duct, or vessel. Catheters are configured to allow fluid drainage, to permit administration of fluids or gases, and/or to allow access by surgical instruments, depending on the particular catheter type. In many implementations, a catheter is a thin, flexible tube (which may be referred to as a "soft" catheter), although catheters may have varying levels of stiffness depending on the application. A catheter left inside the body for a long period of time, or permanently, may be referred to as an "indwelling catheter." Conversely, a catheter inserted temporarily or for a short period of time may be referred to as an "intermittent catheter."

It would be advantageous to treat the surface of a medical device using a process which enables different densities of coating and different functionalizations to be achieved.

SUMMARY

The present disclosure may comprise one or more of the following features and combinations thereof.

According to one aspect of the present disclosure, a method of modifying a medical device may include functionalizing a surface of the medical device using cold plasma.

In some embodiments, functionalizing the surface using cold plasma may include contacting the surface with cold plasma to provide a plasma-treated surface and functionalizing the plasma-treated surface with a polymer.

In some embodiments, contacting the surface with cold plasma may include introducing a monomer to cold plasma to create monomer plasma and applying the monomer plasma to the surface to provide the plasma-treated surface.

In some embodiments, functionalizing the plasma-treated surface with the polymer may include plasma polymerizing the monomer plasma onto the plasma-treated surface.

In some embodiments, the method may include mixing the monomer with a precursor fluid or plasma gas selected from the group including hydrogen, oxygen, nitrogen, air, ammonia, argon, helium, carbon dioxide, water, methane, ethane, propane, butane, or any mixture thereof.

In some embodiments, contacting the surface with cold plasma may include treating the surface with cold plasma to create reactive sites or polymerization initiation sites on the surface.

In some embodiments, functionalizing the plasma-treated surface with the polymer may include reacting, simultaneously or subsequently, a polymer or a monomer with the plasma-treated surface to functionalize the surface with the polymer or the monomer.

In some embodiments, the cold plasma may include a plasma fluid or plasma gas selected from the group including hydrogen, oxygen, nitrogen, air, ammonia, argon, helium, carbon dioxide, water, methane, ethane, propane, butane, or any mixture thereof.

In some embodiments, the method may include creating a hydrophilic surface or a hydrophobic surface.

In some embodiments, the polymer or the monomer may be a polyalkylene glycol having a reactive end group.

In some embodiments, the polymer or the monomer may be selected from the group including an acrylate-functionalized polyalkylene glycol and an alkylacrylate polyalkylene glycol.

In some embodiments, the polymer or the monomer may be selected from the group including an acrylate- or methacrylate-functionalized polyethylene or polypropylene glycol.

In some embodiments, the polymer may be selected from the group including a linear polymer, a branched polymer, a dendritic polymer, a star polymer, a dendronized polymer, a comb polymer, a polymer brush, or a ladder polymer.

In some embodiments, functionalizing the surface of the medical device using cold plasma may include performing cold plasma treatment at a pressure of between 0.5 and 1500 mbar.

In some embodiments, functionalizing the surface of the medical device using cold plasma may include performing cold plasma treatment at a temperature of between 0° C. and 60° C.

In some embodiments, functionalizing the surface of the medical device using cold plasma may include performing cold plasma treatment at a temperature of between 15° C. and 40° C.

In some embodiments, functionalizing the surface of the medical device using cold plasma may include performing cold plasma treatment at a plasma power of between 1 W and 2000 W.

In some embodiments, functionalizing the surface of the medical device using cold plasma may include performing cold plasma treatment at a plasma power of between 5 W and 100 W.

In some embodiments, the medical device may be an intermittent catheter.

According to another aspect of the present disclosure, a method of modifying a medical device may include combining a monomer with a cold plasma, creating a monomer plasma of the monomer, and graft polymerizing the monomer plasma onto a surface of the medical device.

According to yet another aspect of the present disclosure, a medical device may be obtained by any method disclosed herein.

According to yet another aspect of the present disclosure still, a method of modifying a medical device may include combining a monomer with a cold plasma, creating a monomer plasma of the monomer, and graft polymerizing the monomer plasma onto a surface of the medical device to create a hydrophilic surface or a hydrophobic surface. Combining the monomer with the cold plasma may include mixing the monomer with a precursor fluid or plasma gas selected from the group including hydrogen, oxygen, nitrogen, air, ammonia, argon, helium, carbon dioxide, water, methane, ethane, propane, butane, or any mixture thereof.

In some embodiments, graft polymerizing the monomer plasma onto the surface of the medical device may include creating a hydrophilic surface.

In some embodiments, graft polymerizing the monomer plasma onto the surface of the medical device may include creating a hydrophobic surface.

In some embodiments, the monomer may be a polyalkylene glycol having a reactive end group.

In some embodiments, the monomer may be selected from the group including an acrylate-functionalized polyalkylene glycol and an alkylacrylate polyalkylene glycol.

In some embodiments, the monomer may be selected from the group including an acrylate- or methacrylate-functionalized polyethylene or polypropylene glycol.

These and other features of the present disclosure will become more apparent from the following description of the illustrative embodiments.

DETAILED DESCRIPTION

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features, such as those representing devices, modules, instructions blocks and data elements, may be shown in specific arrangements and/or orderings for ease of description. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

In some embodiments, schematic elements used to represent blocks of a method may be manually performed by a user. In other embodiments, implementation of those schematic elements may be automated using any suitable form of machine-readable instruction, such as software or firmware applications, programs, functions, modules, routines, processes, procedures, plug-ins, applets, widgets, code fragments and/or others, for example, and each such instruction may be implemented using any suitable programming language, library, application programming interface (API), and/or other software development tools. For instance, in some embodiments, the schematic elements may be implemented using Java, C++, and/or other programming languages. Similarly, schematic elements used to represent data or information may be implemented using any suitable electronic arrangement or structure, such as a register, data store, table, record, array, index, hash, map, tree, list, graph, file (of any file type), folder, directory, database, and/or others, for example.

Further, in the drawings, where connecting elements, such as solid or dashed lines or arrows, are used to illustrate a connection, relationship, or association between or among two or more other schematic elements, the absence of any such connection elements is not meant to imply that no connection, relationship, or association can exist. In other words, some connections, relationships, or associations between elements may not be shown in the drawings so as not to obscure the disclosure. In addition, for ease of illustration, a single connecting element may be used to represent multiple connections, relationships, or associations between elements. For example, where a connecting element represents a communication of signals, data or instructions, it should be understood by those skilled in the art that such element may represent one or multiple signal paths (e.g., a bus), as may be needed, to effect the communication.

An intermittent catheter may be inserted into the bladder through the urethra to drain the bladder of urine before being removed. In those uses, one end of the catheter is typically either left open-ended (e.g., to allow drainage into a suitable receptacle) or attached to a urine collection bag, while the other end is guided through the urethra to the bladder. A sterile catheter intended for insertion into a conscious patient is usually pre-lubricated to avoid discomfort and facilitate smooth guidance of the catheter against internal body tissue. In some cases, pre-lubrication may be achieved with a lubricious coating while ensuring that the lubricious coating cannot be removed through friction or absorption before insertion of the catheter into the urethra.

Lubricity of a surface may be achieved by rendering the surface either hydrophilic (e.g., followed by wetting) or hydrophobic. The degree of hydrophilicity or hydrophobicity of a surface may be assessed by measuring the contact angle between an aqueous liquid and a solid surface. Hydrophobic materials, such as non-polar materials, for example, demonstrate a low affinity to water such that those materials are water repelling. In some cases, a contact angle of less than 90° indicates hydrophilicity whereas a contact angle greater than 90° indicates a hydrophobicity. It should be appreciated that hydrophilic or hydrophobic agents may be applied to surfaces to modify surface material properties and provide a particular degree of hydrophilicity or hydrophobicity.

In at least one aspect, the present disclosure is directed a method of modifying a medical device (e.g., at least part of a surface of a medical device) that includes functionalizing, with a polymer, a surface of the medical device using cold plasma. For the purposes of the present disclosure, cold plasma, which may be referred to as non-thermal or non-equilibrium plasma, is the term used to describe cold temperature plasma formation at atmospheric pressure(s). It should be appreciated that cold plasma is a plasma not in thermodynamic equilibrium because the temperature of electron(s) in the plasma is significantly hotter than the temperature of heavy species (e.g., ions and neutrals) in the plasma.

In many cases, cold plasma is created when a sufficient amount of energy (i.e., greater than the ionization energy) is added to gaseous atoms and/or molecules, which causes ionization and subsequently generates free electrons, photons, free radicals, and ionic species. The excitation energy supplied to a gas to form a cold plasma may originate from electrical discharges, direct currents, radio frequencies, microwaves, or other forms of electromagnetic radiation, just to name a few. Non-limiting examples of cold plasma technologies and methodologies for generating cold plasma include atmospheric pressure plasma jet, dielectric barrier discharge, direct current (DC) glow discharge, electrical discharge plasma, microwave discharge, pulsed power discharge, radiofrequency (RF) discharge, and the like. In any case, it should be appreciated that by selecting the reaction conditions accordingly (e.g., activation and/or excitation energy, pressure, temperature, carrier gases, power input, and initial organic compounds such as polymer or monomers), suitable modified surfaces can be created for different applications or requirements.

In at least some embodiments, the methods of the present disclosure are directed to modifying the surface of a medical device to provide a lubricious surface. In some embodiments, modifying the surface of the medical device includes creating a hydrophilic or a hydrophobic surface. Additionally, in some embodiments, the medical device is an intermittent catheter. In some embodiments still, the surface is an outer surface of the medical device.

In some embodiments, the methods of the present disclosure are directed to modifying the whole surface, or substantially the whole surface, of a medical device. It should be appreciated that in at least some embodiments, "substantially the whole surface" refers to a small amount of unmodified surface area, preferably less than 5% of the total surface area. In some cases, "substantially the whole surface" refers to less than 0.5% of the total surface area that is unmodified.

In some embodiments, a method of modifying a medical device in accordance with the present disclosure may include (a) contacting and/or treating a surface of a medical device with cold plasma to provide a plasma-treated surface and (b) functionalizing the plasma-treated surface with the polymer. In some embodiments, features (a) and (b) may be performed simultaneously. In such embodiments, the method may include contacting and/or treating a surface of the medical device with a polymer or a monomer dispersed in a cold plasma stream to cause polymerization of the monomer or graft polymerization of the polymer, thereby resulting in functionalization in the plasma-treated surface. In other embodiments, feature (b) may be performed subsequent to feature (a). In such embodiments, feature (b) may include, or otherwise be embodied as, polymerizing the monomer or graft polymerizing the polymer.

In some embodiments, feature (a) includes treating the surface with cold plasma to create reactive sites (e.g., polymer initiation sites) on the surface. Additionally, in some embodiments, feature (b) includes simultaneously or subsequently grafting a polymer onto the reactive sites of the surface to functionalize the surface with the polymer. In other embodiments, feature (a) includes treating the surface with cold plasma to create reactive sites (e.g., polymer initiation sites) on the surface, and feature (b) includes simultaneously or subsequently polymerizing a monomer on the reactive sites of the surface to functionalize the surface. Furthermore, in some embodiments, the polymer may be covalently bonded to the surface of the medical device.

In some embodiments, feature (b) may include reacting the plasma-treated surface with a hydrophilic or hydrophobic polymer. Additionally, in some embodiments, feature (b) may include forming a hydrophilic or hydrophobic polymer on the surface. Further still, in some embodiments, feature (b) may include reacting the plasma-treated surface with more than one polymer, one or more co-polymers, and/or more than one monomer.

In some embodiments, the method of modifying the medical device may be a method of hydrophilizing the surface. In such embodiments, feature (b) includes reacting the plasma-treated surface with a hydrophilic functional group-containing polymer or monomer. In one example, the hydrophilic polymer or monomer may include a polymer or monomer selected from the group including an ethylenically-unsaturated polymer with hydrophilic, charged, or polar functional groups, a polyalkylene glycol polymer, an acrylate or methacrylate polymer with hydrophilic, charged, or polar functional groups, and an N-vinyl lactam.

When monomer(s) are used to functionalize the surface of the medical device, the monomer may be applied subsequently to the cold plasma as indicated above. In that situation, the plasma may create a reactive surface which on which the monomer or monomer plasma is subsequently grafted or reacted. Alternatively, the monomer may be dispersed in the cold plasma stream and applied simultaneously to the surface followed by polymerization.

In accordance with the teachings of the present disclosure, particularly favorable results have been obtained with using polyalkylene glycol polymers and monomers for the surface functionalization. In one example, polyalkylene glycol polymers or monomers having 1 to 8 carbons in the alkyl chain, particularly polyethylene glycol and polypropylene glycol, have been found to provide effective surface modification and functionalization. Those polymers or monomers may be easily grafted to, or polymerized onto, cold-plasma treated surfaces to create an effective hydrophilic surface that, when wetted, provides excellent lubricity to the surface of the medical device, particularly catheters.

In some embodiments, the polyalkylene glycol polymer or monomer includes a reactive end group. Additionally, in some embodiments, the hydrophilic polymer or monomer is an acrylate-, methacrylate-, or ethacrylate-functionalized polyalkylene glycol. Further, in some embodiments still, the hydrophilic polymer or monomer is an acrylate-functionalized or methacrylate-functionalized polyethylene glycol or polypropylene glycol, particularly poly(ethylene glycol) methyl ether acrylate.

In some embodiments, the polyalkylene glycol polymer or monomer, such as polyethylene glycol or polypropylene glycol, for example, has a molecular weight (Mw) of no more than 10,000. Additionally, in some embodiments, the molecular weight of the polyalkylene glycol polymer or monomer is no more than 5000, 2500, 1500, or 1000. In some embodiments still, the polyalkylene glycol polymer or monomer includes polyethylene glycol or polypropylene glycol having a molecular weight of between 100 and 1000, such as between 100 and 800, and in particular 200-400.

In some embodiments, the polyalkylene glycol polymer may have any suitable reactive end group, such as an end group selected from the group including epoxy, vinyl, thiol, silane, aldehyde, amine, azide, biotin, carboxylic acid, fluorescent, halide, hydrazide, hydroxyl, lipid, maleimide, norborene, alkyne, olefin, phosphate, pyrene, sulfonate, or vinyl sulfone, for example. In other embodiments, the polyalkylene glycol (PAG) monomer or polymer may be selected from the group including a 4-arm PAG, 8-arm PAG, amphiphilic PAG, heterobifunctional PAG, homobifunctional PAG, hyperbranched dendrimer PAG, methoxylinear PAG, and monodisperse PAG.

In some embodiments, a method of modifying a medical device according to the teachings of the present disclosure is a method of hydrophobicizing the surface of the medical device. In such embodiments, feature (b) discussed above includes reacting the plasma-treated surface with a hydrophobic functional group-containing polymer or monomer. Further, in some embodiments, the hydrophobic functional group-containing polymer or monomer includes a compound selected from the group including a hydrophobic acrylate, a hydrophobic methacrylate, a hydrophobic silane, and polytetrafluoroethylene.

In some embodiments, the polymerization effected in feature (b) is carried out by plasma induced graft polymerization (PIGP). In such embodiments, the surface may be activated using cold plasma to create initiation sites or points, and in those cases, a polymer or monomer in liquid or gas phase may be subsequently grafted to the initiation sites or points through a free radical grafting mechanism. This approach may produce, or otherwise be associated with, a grafted polymer phase characterized by a high surface density of the polymer chains initiated and polymerized directly from the substrate surface.

In some embodiments, the polymer is selected from the group including a linear polymer, a branched polymer, a dendritic polymer, a star polymer, a dendronised polymer, a comb polymer, a polymer brush, and a ladder polymer. Additionally, in some embodiments, the polymer is grafted onto the surface of the medical device.

In some embodiments, the cold plasma is formed from, or otherwise includes, a precursor (or plasma) fluid and/or gas selected from the group including hydrogen, oxygen, nitrogen, air, ammonia, argon, helium, carbon dioxide, water, methane, ethane, propane, or butane or any mixture thereof. In some configurations, the precursor gas may be carried by a carrier gas, which may be the same gas as the precursor gas. In one example, the carrier gas may be an inert gas such as argon, for example.

In some embodiments, a method of modifying a medical device includes introducing a monomer to cold plasma to create a monomer plasma and plasma polymerizing the plasma monomer onto the surface to provide the plasma-treated surface. In some cases, plasma polymerizing the plasma monomer onto the surface includes plasma polymerizing more than one plasma monomer onto the surface.

In some embodiments, the monomer is added to, and/or mixed with, a stream of plasma gas or carrier gas. Additionally, in some embodiments, the monomer is mixed with a precursor (or plasma) fluid and/or gas selected from the group including hydrogen, oxygen, nitrogen, air, ammonia, argon, helium, carbon dioxide, water, methane, ethane, propane, butane or any mixture thereof. Further, in some embodiments, the monomer plasma is mixed with a carrier gas, which may be selected from the group including hydrogen, oxygen, nitrogen, air, ammonia, argon, helium, carbon dioxide, water, methane, ethane, propane, butane, or any mixture thereof. Further still, in some embodiments, the carrier gas is an inert gas such as argon, for example.

At least in some embodiments, the monomer is an ethylenically unsaturated monomer. Additionally, in some embodiments, the monomer is selected from the group including an acid vinyl monomer, an acrylic or methacrylic ester, a polar vinyl monomer, or a non-polar vinyl monomer. To create a hydrophilic surface, at least in some embodiments, the monomer includes a polyalkylene glycol monomer having 1 to 8 carbons in the alkyl chain. In particular, the monomer includes a polyethylene glycol or a polypropylene glycol monomer, at least in some cases. As indicated above, those monomers may be easily grafted to, or polymerized onto, cold-plasma treated surfaces to create an effective hydrophilic surface that, when wetted, provides excellent lubricity to the surface of the medical device, particularly catheters.

The polyalkylene glycol monomer (e.g., the polyethylene glycol monomer or the polypropylene glycol monomer) has a molecular weight (Mw) of no more than 10,000, at least in some embodiments. Additionally, in some embodiments, the molecular weight of the polyalkylene glycol monomer is no more than 5000, 2500, 1500, or 1000. Further, in some embodiments still, the polyalkylene glycol monomer includes, or is otherwise embodied as, a polyethylene glycol monomer or a polypropylene glycol monomer having a molecular weight of between 100 and 1000, such as between 100 and 800, and especially 200-400.

In some embodiments, the polyalkylene glycol monomer may have any suitable reactive end group, such as an end group selected from the group including epoxy, vinyl, thiol, silane, aldehyde, amine, azide, biotin, carboxylic acid, fluorescent, halide, hydrazide, hydroxyl, lipid, maleimide, norborene, alkyne, olefin, phosphate, pyrene, sulfonate, or vinyl sulfone, for example. In other embodiments, the polyalkylene glycol (PAG) monomer or polymer may be selected from the group including a 4-arm PAG, 8-arm PAG, amphiphilic PAG, heterobifunctional PAG, homobifunctional PAG, hyperbranched dendrimer PAG, methoxylinear PAG, and monodisperse PAG.

It should be appreciated that polymerization of the surface in any of the embodiments described herein may occur by any suitable polymerization process, such as condensation, addition or free radical graft polymerization (FRGP), or controlled radical polymerization (CRP), for example. Types of CRP contemplated herein include, but are not limited to, ATRGP, RAFT, and NMGP. The surface activity may be controlled by adjusting plasma operating parameters and other parameters including the plasma source, the plasma precursor and carrier gas, gas flow rate, gas partial pressure, high frequency power, and applied voltage, as well as the surface treatment time and substrate surface, among others.

In some embodiments, the cold plasma utilized for polymerization is cold atmospheric plasma (CAP). The cold plasma may be an atmospheric pressure discharge cold plasma, at least in some embodiments. Additionally, in some embodiments, the cold atmospheric plasma may be at a pressure of between around 50 kPa and 150 kPa. Further, in some embodiments, the cold atmospheric plasma may be at a pressure of between around 60 kPa and 140 kPa. In some embodiments, the cold atmospheric plasma may be at a pressure of between around 70 kPa and 130 kPa. Further still, in some embodiments, the cold atmospheric plasma may be at a pressure of between around 80 kPa and 120 kPa. Finally, in some embodiments, the cold atmospheric plasma may be at a pressure of between around 100 kPa and 103 kPa. Of course, it should be appreciated that in some embodiments, the cold atmospheric plasma may be applied under reduced pressure, such as between 0.01 kPa and 40 kPa, or between 0.1 kPa and 25 kPa, for example.

In some embodiments, a cold plasma stream is applied to the surface to cause formation of surface-bound active sites that function as polymerization initiators or covalent binding sites. In such embodiments, when contacted with a polymer, monomer, or monomer solution, the active sites may facilitate formation of a dense array of graft polymers covalently bound to the substrate surface.

In some embodiments, the surface of the medical device (e.g., the substrate surface) may be placed either directly in contact with the plasma as it is generated, or in a separate post-plasma area. If the surface is placed directly in contact with the plasma during generation thereof, that contact may occur in a plasma reactor or other suitable environment. For the purposes of the present disclosure, post-plasma (post-discharge) area refers to an area located outside of the plasma and downstream of a plasma forming gas flow introduced into the plasma in which reactive species (e.g., radicals) are still present. It should be appreciated that the post-plasma area is particularly useful for delicate substrate surfaces such as polymers.

In some embodiments, the cold plasma treatment may be performed at an RF output power of at least 1 W, 5 W, 10 W, 15 W, or at least 20 W. Additionally, in some embodiments, the cold plasma treatment may be performed at an RF output power of no more than 2000 W, 1500 W, 1000 W, 500 W, 400 W, 300 W, 200 W, 100 W, 90 W, 80 W, 70 W, or no more than 60 W. In some embodiments still, the treatment may be performed at an RF output power of about 20 to 60 W.

In some embodiments, the temperature of the cold plasma may be at least 5° C., or at least 10° C. Additionally, in some embodiments, the temperature of the cold plasma may be no more than 60° or no more than 50° C. In some embodiments still, the cold plasma may be at ambient temperature, such as between 15° C. and 35° C., for example.

In some embodiments, the cold plasma treatment may be performed for at least 1 second, 2 seconds, 3 seconds, 4 seconds, 5 seconds, or at least 10 seconds. Additionally, in some embodiments, the cold plasma treatment may be performed for no more than 240 seconds, no more than 180 seconds, or no more than 120 seconds. In some embodiments still, the treatment may be performed for about 5 to 120 seconds.

In some embodiments, the cold plasma treatment may be performed at an RF output power of between about 10 W to about 60 W and for a period of between about 5 seconds to about 1200 seconds, and the treatment may be performed using a precursor gas selected from the group including hydrogen, oxygen, nitrogen, argon, or helium. Additionally, in some embodiments, the surface of the medical device may include a polymer selected from the group including polyolefins, vinyl polymers, synthetic or natural elastomers, silicone, polyether, amide, polyurethane, fluoropolymers (e.g., PTFE), and co-polymers thereof.

The following describe particular embodiments of the invention by way of example only.

Example 1

Acrylate-functionalized polyethylene glycol having Formula I below (Sigma-Aldritch, UK) and a molecular weight of 400 (hereinafter "AFPEG") was dispersed into a nitrogen gas stream.

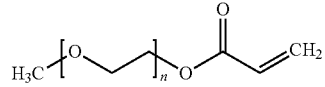

Formula I

The AFPEG was combined with cold, atmospheric nitrogen plasma, which was generated in a direct barrier discharge (DBD) reactor using an electromagnetic field generated by a high-frequency AC power source, to create a AFPEG monomer plasma. The reactive AFPEG monomer plasma was then directed onto the surface of a polyolefinic thermoplastic elastomer (TPE) intermittent catheter (Convatec, Ltd, Deeside, UK), which underwent plasma polymerization to modify the surface of the catheter with hydrophilic AFPEG moieties.

The plasma device used in this example was a bespoke stainless-steel reactor with two symmetric internal parallel-plate electrodes. The plasma was generated by a radio frequency (RF) generator (13.56 MHz) connected to the upper electrode, whereas the bottom electrode was grounded and used as the sample holder. AFPEG monomer flow rate was controlled to a constant monomer flow rate of 1.5 cm$^3$ per min at a plasma power of 30 W. Depositions took place for a period of 10 minutes.

A mixture of AFPEG vapour and nitrogen was used as gas feed for the deposition of PEG films. Gas flow rates were regulated mass-flow controllers and the pressure was monitored by a baratron. The low pressure in the chamber was maintained by a rotary pump. Between each deposition, the plasma chamber was cleaned for 30 min by a pure oxygen plasma (15 W) followed by 10 min of a pure argon plasma (10 W).

Plasma polymerization was done at temperatures of <35° C. After being synthesized, samples were soaked in de-ionized water for 24 hours in order to remove any non-reacted material, and thereafter dried with nitrogen. The PEG functionalized TPE catheter surfaces were found to be hydrophilic, attracting water when wetted and forming a lubricious coating, which aided in insertion into urethras.

Example 2

Acrylate-functionalized polyethylene glycol of Formula I (see Example 1) was again dispersed into a nitrogen gas stream. Cold argon plasma was used on the surface of a TPE intermittent catheter (Convatec Ltd, UK) to create polymerization initiation sites. Subsequently, the acrylate-functionalized polyethylene glycol was directed onto the cold plasma treated surface of the TPE catheter and the plasma-activated surface reacted with the PEG species, creating covalent bonds and yielding chemically functionalized TPE surface with PEG moieties. Again, the PEG functionalized TPE catheter surface was found to be hydrophilic, attracting water when wetted and forming a lubricious coating, which aided in insertion into urethras.

Lubricity characteristics (e.g., coefficient of friction measurements) were measured for various functionalized catheters. The results are summarized in Table 2 below.

TABLE 2

| Rep | GC Glide | SpeediCath Compact Eve | Infyna Chic | LoFric Elle | Magic 3 | CompactCath Lite | CureTwist | CureUltra | Emteva Pure |
|---|---|---|---|---|---|---|---|---|---|
| 1 | 0.0507 | 0.0101 | 0.0243 | 0.0457 | 0.1164 | 0.6280 | 0.1886 | 0.3170 | 0.2656 |
| 2 | 0.0567 | 0.0126 | 0.0227 | 0.0375 | 0.1314 | 0.3142 | 0.1804 | 0.3892 | 0.3336 |
| 3 | 0.0588 | 0.0114 | 0.0267 | 0.0366 | 0.0926 | 0.4318 | 0.1932 | 0.3426 | 0.3372 |
| 4 | 0.0573 | 0.0104 | 0.0240 | 0.0358 | 0.1014 | 0.4400 | 0.2254 | 0.6554 | 0.3220 |
| 5 | 0.0574 | 0.0113 | 0.0267 | 0.0357 | 0.1062 | 0.2662 | 0.2114 | 0.3146 | 0.3880 |
| 6 | 0.0569 | 0.0112 | 0.0245 | | 0.1080 | 0.2420 | 0.2058 | 0.3682 | 0.3724 |
| 7 | 0.0592 | 0.0135 | 0.0308 | | 0.1018 | 0.2202 | 0.2120 | 0.4380 | 0.2770 |
| 8 | 0.0563 | 0.0088 | 0.0344 | | 0.1030 | 0.2156 | 0.2184 | 0.5600 | 0.3576 |
| 9 | 0.0597 | 0.0121 | 0.0377 | | 0.0980 | 0.5012 | 0.2168 | 0.4270 | 0.3830 |
| 10 | 0.0588 | 0.0107 | 0.0214 | | 0.1278 | 0.2422 | 0.1956 | 0.4140 | 0.3098 |
| 11 | 0.0614 | | | | | | 0.2100 | | |
| 12 | 0.0563 | | | | | | 0.2302 | | |
| 13 | 0.0622 | | | | | | 0.2446 | | |
| 14 | 0.0578 | | | | | | 0.2386 | | |
| 15 | 0.0556 | | | | | | 0.2368 | | |
| 16 | 0.0644 | | | | | | 0.2060 | | |
| 17 | 0.0585 | | | | | | 0.2200 | | |
| 18 | | | | | | | 0.2524 | | |
| 19 | | | | | | | 0.1864 | | |
| 20 | | | | | | | 0.2534 | | |
| Mean | 0.0581 | 0.0112 | 0.0273 | 0.0383 | 0.1087 | 0.3501 | 0.2163 | 0.4226 | 0.3346 |
| SD | 0.003 | 0.001332 | 0.00533 | 0.00422 | 0.01271 | 0.14198466 | 0.02165 | 0.10888 | 0.04218 |
| % RSD | 5.17 | 11.88 | 19.49 | 11.03 | 11.69 | 40.55 | 10.01 | 25.76 | 12.61 |

As shown in Table 2, the average coefficient of friction result observed for emteva pure is 0.3346 compared to 0.0581 for GentleCath Glide. Additionally, the variability of the data set is greater; % RSD of 11.96% compared to 5.17% for GentleCath Glide.

Results demonstrate superior lubricity for GentleCath Glide. The maximum specification limit for coefficient of friction for GentleCath Glide finished product is 0.17. All test replicates observed for emteva pure are above this limit.

After COF testing the ten samples were put into beakers of water that were agitated for 30 minutes using magnetic peas and a magnetic stirrer. Upon the ending of the 30 minutes, it was noticed that there were no obvious signs of biodegradation and it was decided to leave the samples in the beakers with water for 7 days, water was added if the water level dropped below the required level to fully submerge the samples. Images taken over this 7 day period are shown in FIG. 2.

The data collected shows that GentleCath Glide demonstrates superior catheter lubricity when compared to emteva pure when tested using the Harland Friction Tester. As shown in FIG. 2, after 7 days of being placed in water the catheter has not decomposed.

As shown in Table 2, the average coefficient of friction result observed for CureUltra is 0.4226 compared to 0.0581 for GentleCath Glide. Additionally, the variability of the data set is considerably greater; % RSD of 25.76% compared to 5.17% for GentleCath Glide.

Results demonstrate superior lubricity for GentleCath Glide. The maximum specification limit for coefficient of friction for GentleCath Glide finished product is 0.17. All test replicates observed for CureUltra fall above this limit.

It is concluded that GentleCath Glide demonstrates superior catheter lubricity when compared to CureUltra when tested using the Harland Friction Tester.

Lubricity characteristics (e.g., coefficient of friction measurements, water contact angle) were measured for various functionalized catheters. The results are summarized in Table 3 below.

TABLE 3

| Sample | substrate | Precursor | Power [W] | Gas type | Total flow [slm] | Precursor flow [slm] | Dilution flow [slm] | Length (cm) | Passes | WCA [°] | COF |
|---|---|---|---|---|---|---|---|---|---|---|---|
| untreated control | rougher tube | N/A | N/A | N/A | N/A | N/A | N/A | N/A | N/A | 83 | 0.98 |
| 9 | rougher tube | PEG 400/ EGDMA | 350 | N2 | 80 | 1.2 | 5 | 16 | 3 b-a-f | 45 | 0.8 |
| 10 | rougher tube | PEG 400/ EGDMA | 350 | N2 | 80 | 1.2 | 5 | 16 | 6 b-a-f | 33 | 0.67 |
| 11 | rougher tube | PEG 400/ EGDMA | 350 | N2 | 80 | 1.2 | 5 | 16 | 12 b-a-f | 18 | 0.91 |
| 13 | rougher tube | PEGMA/ EGDMA | 350 | N2 | 80 | 0.7 | 5 | 16 | 3 b-a-f | 31 | 0.79 |
| 14 | rougher tube | PEGMA/ EGDMA | 350 | N2 | 80 | 0.7 | 5 | 16 | 6 b-a-f | 20 | 0.73 |
| 15 | rougher tube | PEGMA/ EGDMA | 350 | N2 | 80 | 0.7 | 5 | 16 | 12 b-a-f | 25 | 0.67 |
| untreated control | smoother tube | N/A | N/A | N/A | N/A | N/A | N/A | N/A | N/A | 60-75 | ? |
| 1A | smoother tube | PEG 400/ EGDMA | 350 | N2 | 80 | 1.2 | 5 | 16 | 12 b-a-f | 19 | 0.37 |

TABLE 3-continued

| Sample | substrate | Precursor | Power [W] | Gas type | Total flow [slm] | Precursor flow [slm] | Dilution flow [slm] | Length (cm) | Passes | WCA [°] | COF |
|---|---|---|---|---|---|---|---|---|---|---|---|
| 3A | smoother tube | PEGMA/ EGDMA | 350 | N2 | 80 | 0.7 | 5 | 16 | 12 b-a-f | 23-24 | 0.56 |
| 4A | smoother tube | PEGMA/ EGDMA | 350 | N2 | 80 | 0.8 | 5 | 16 | 6 b-a-f | 18-19 | 0.42 |
| GC glide | N/A (finished product) | | N/A | N/A | N/A | N/A | N/A | N/A | N/A | 30 | 0.058 |

3EGDVE = Tri(ethylene glycol) divinyl ether (CAS 765-12-8)
EGDMA = Ethylene glycol dimethacrylate (CAS 97-90-5)
PEG 400 = Poly(ethylene glycol) 400 (CAS 25322-68-3) - to be mixed with EGDMA
PEGMA = Poly(ethylene glycol) methacrylate (CAS 25736-86-1) - to be mixed with EGDMA The following precursors (or formulations) were elected, in agreement with ConvaTec:

3EGDVE=Tri(ethylene glycol) divinyl ether (CAS 765-12-8). Precursor for the plasma deposition of anti-fouling PEG-like coatings. 3 EG units. Vinyl groups tend to enhance grafting and deposition rate.

EGDMA=Ethylene glycol dimethacrylate (CAS 97-90-5). Hydrophilic monomer. Only one EG unit surrounded by methacrylic functions.

PEG 400/EGDMA=50 wt % Poly(ethylene glycol) 400 (CAS 25322-68-3) In EGDMA. On average, 9 EG units. Tends to be poorly grafted when used alone. Here, EGDMA was used as a crosslinker.

PEGMA/EGDMA=50 wt % Poly(ethylene glycol) methacrylate (CAS 25736-86-1) in EGDMA. Very similar to PEG 400, but with an additional functional group (methacrylate) that could enhance grafting to the substrate. EGDMA is also used as a crosslinker.

MPG's PlasmaSpot® equipment was used for all treatments (see FIG. 2). A specific nozzle system, designed and printed by MPG (ref: LD0279/LD0280), enabled uniform treatment of the outer walls of the catheters. The latter were mounted on a rotating (ca. 5 RPM) sample holder system by means of a thin carbon wire passing through the tube. The plasma head was then scanned across the surface to be treated, thereby simulating a dynamic production line.

The plasma power was explored In the case of 3EGDVE (see experimental table above), until it was decided to fix its value to 350 W. This value corresponds to the highest power—for optimal grafting and highest crosslinking degree of the plasma coating—that could be used without damaging the catheters. NOTE: Some tests were performed using a plasma power of 450 W; that resulted in a clearly visible "shrinking" of the treated material.

Line speed was arbitrarily set to 1 m/min, while the number of passes (→coating thickness) was varied.

The mass feed of the precursor was controlled by the "precursor flow" parameter. This parameter was adapted in every case for optimal precursor feed. Nitrogen ($N_2$; 80 slm) was the main plasma and carrier gas.

The power-to-precursor feed ratio, in other words the energy-per-molecule, influences the retention of key chemical moieties (here, EG units) along with the degree of cross-linking. While higher power potentially induces more cross-linked and better grafted plasma-coating, it also leads to more fragmentation of the precursor, thus, a loss of chemical moieties;

Q&D Testing and Comments

Several tests were performed at MPG, during the Discovery Day. A portable water contact angle (WCA) equipment was used to evaluate the hydrophilicity of treated surfaces. These measurements were complemented with a semi-qualitative, ink-based, surface energy evaluation. In addition, as requested by Rachel Pytel, extra sacrificial samples were produced to evaluate the lubricity through a qualitative "feel test" upon wetting.

WCA/SE: The values are reported in the experimental table, for every precursor and condition tested.

Untreated tubes: 83°; Finished product provided by ConvaTec: 30°

3EGDVE at 150 W (low power) led to WCA values around 60°, regardless of the thickness (number of passes). Increasing the power to 300 W had the effect of lowering the value to ca. 46°. That can be tentatively explained by increased fragmentation of the precursor molecules, thus the formation of more radical sites available not only for crosslinking, but also for post-oxidization.

Like 3EGDVE ones, EGDMA-based coatings led to angles in the 60° range. These values were not surprising in view of the low number of EG units in those two precursors. For that reason, precursors with longer EG chains were elected.

PEG 400/EGDMA mix: with this precursor, much more hydrophilic coatings could be achieved, in particular as the thickness of the deposited layer was Increased. 3 passes led to angles around 45°, while 12 passes resulted in very wettable surfaces (18°). The same range of WCA (20-30°) was achieved with the PEGMA/EGDMA mix, although with a less obvious trend with respect to thickness. Overall, this was a clear indication that our process does lead to grafting of the desired chemical moieties at the surface of the catheters.

IMPORTANT NOTE: using the sacrificial samples (see next bullet point), we re-checked the WCA values after wetting-drying of the samples. The measured WCA values remained in the same range as for the freshly-treated ones. This is an indication that the plasma coatings are well-grafted, and do not release/dissolve upon humidification and contact with fingers or, to the least, not completely.

Qualitative "feel" test: as suggested by ConvaTec, extra sacrificial samples were produced. These were soaked in water and the lubricity was evaluated with bare hands. In a very qualitative fashion. Conditions that have been tested were all given a "poor lubricity" rate (see experimental table), meaning that the roughness of the additive-free tubes was still very present in spite of plasma treatment. However, samples prepared with PEG 400/EGDMA and PEGMA/EGDMA exhibited a slightly improved slipperiness—unfortunately, not yet close to the one of the finished product. The color code in the experimental table expresses our overall feeling of the proposed plasma solution. Red stands for samples that are not sufficiently hydrophilic and slippery; orange stands for samples that were not judged sufficiently slippery—although slightly better—, but for which surface wettability was satisfactory or close to the target (30° for ConvaTec's finished product).

Roughness: in an attempt to understand the reasons for unsatisfactory slipperiness in spite of satisfactory surface wettability, we used a microscope to observe and compare the surfaces of additive-free (bare or plasma-treated) and "finished product" tubes, respectively appeared that additive-free samples have a relatively rough surface (regardless of plasma treatment), while finished product ones are very smooth. This could be one of the major obstacles in achieving high lubricity with plasma coatings. Indeed, our technology enables the deposition of very thin coatings, in the 10-100 nm range, far below the intrinsic roughness of the material.

Conclusions

Successful deposition of PEG-like moieties, that in some cases (depending on the deposited chemistry and plasma parameters) led to high and persistent wettability of the treated surfaces was demonstrated.

Regrettably, none of the tested chemistries and conditions led to satisfactory lubricity, something that was assessed only very qualitatively.

One possible reason for the poor lubricity may be the obvious intrinsic roughness of the untreated tubes. In comparison, "finished product" ones are much smoother. Even for longer treatment times (trials with up to 30 passes were performed, see experimental table), the thickness of the plasma coatings is expected to be in the 10-100 nm.

Samples to be tested at ConvaTec have been produced in triplicates, using 4 different chemistries, and 3 different plasma parameters per chemistry—highlighted in green in the sample identification, see experimental table. The total amount (36) of delivered samples is a bit lower than expected, but it has to be taken into account the many "sacrificial" ones that were produced in an attempt to circumvent the roughness problem.

Experimental

The following formulations were elected, in agreement with ConvaTec:
PEG 400/EGDMA=50 wt % Poly(ethylene glycol) 400 (CAS 25322-68-3) In EGDMA. On average, 9 EG units. Tends to be poorly grafted when used alone. Here, EGDMA was used as a crosslinker.
PEGMA/EGDMA=50 wt % Poly(ethylene glycol) methacrylate (CAS 25736-86-1) In EGDMA. Very similar to PEG 400, but with an additional functional group (methacrylate) that could enhance grafting to the substrate. EGDMA is also used as a crosslinker.
MPG's PlasmaSpot® equipment was used for all treatments (see FIG. 2). As in the first series, a specific nozzle system, designed and printed by MPG (ref: LD0279/ LD0280), enabled uniform treatment of the outer walls of the catheters. The latter were mounted on a rotating (ca. 5 RPM) sample holder system by means of a thin carbon wire passing through the tube. The plasma head was then scanned across the surface to be treated, thereby simulating a dynamic production line.
The plasma power was fixed to 350 W. This value corresponds to the highest power—for optimal grafting and highest crosslinking degree of the plasma coating—that could be used without damaging the catheters. NOTE: In the first series, some tests were performed using a plasma power of 450 W; that resulted in a clearly visible "shrinking" of the treated material.
Line speed was arbitrarily set to 1 m/min, while the number of passes (→coating thickness) was varied (12 back-and-forth to 6).
The plasma and carrier gas was $N_2$. Plasma gas flow and dilution flow were set to standard values. 80 slm and 5 slm respectively. The mass feed of the precursor was controlled by the "precursor flow" parameter. The latter was set according to the first series of experiments except for condition 4, where the value was increased from 0.7 to 0.8 in an attempt to further increase the lubricity of the treated tubes (see experimental table).
The power-to-precursor feed ratio, in other words the energy-per-molecule, influences the retention of key chemical moieties (here, EG units) along with the degree of cross-linking. While higher power potentially induces a more cross-linked and better grafted plasma-coating, it also leads to more fragmentation of the precursor, thus, a loss of chemical moieties. FIG. 1, hereunder, schematizes this phenomenon.

Q&D Testing and Comments

Several tests were performed at MPG, during this second Discovery Day. A portable water contact angle (WCA) equipment was used to evaluate the hydrophilicity of treated surfaces. In addition, as requested by Rachel Pytel, extra sacrificial samples were produced to evaluate the lubricity through a qualitative "feel test" upon wetting.
WCA: The values are reported in the experimental table, for every formulation and condition tested.
Untreated tubes: 60-75° (quite variable); Formed catheters: 45-50°; Finished product provided by ConvaTec: 30°. It was quite surprising to see that untreated straight tubes had a quite variable wettability. Also, formed catheters were more wettable than the straight tubes. FIG. 3 compares micrographs of (left) a straight tube and (right) a formed catheter. A slight difference could be seen: the formed catheter appeared to be slightly smoother. NOTE: the finished product appeared even smoother (see first report).
PEG 400/EGDMA mix: in agreement with the first series of test with this formulation, very hydrophilic coatings could be achieved, in particular with straight tubes (samples 1A), where the measured WCA was 19°. Surprisingly, the WCA was higher in the case of formed tubes (samples 1B). 30°. Many samples were tested, all of which confirmed the 30° value. Deeper surface analysis would need to be performed in order to understand this unexpected difference between samples 1A and 1B.
PEGMA/EGDMA mix: all samples plasma-treated with this formulation were all very hydrophilic (16-24° range). Increasing the precursor mass feed (while decreasing the number of passes ↔ thickness) led to an observable decrease in the WCA of the treated straight tubes (3A vs 4A). This was not observed in the case of formed catheters (3B vs 4B) for which both conditions resulted in WCA around 17°.

IMPORTANT NOTE: as in the first series of trials, using the sacrificial samples (see next bullet point), we re-checked the WCA values after wetting-drying of the samples. The measured WCA values remained in the same range as for the freshly-treated ones. This is an indication that the plasma coatings are well-grafted, and do not release/dissolve upon humidification and contact with fingers or, to the least, not completely.

Qualitative "feel" test: as suggested by ConvaTec, extra sacrificial samples were produced for qualitative assessment of lubricity. These were soaked in water and the lubricity was evaluated with bare hands, in a very qualitative fashion.

All treated samples felt fairly more slippery than untreated tubes; this applied to both straight and formed tubes. However, the plasma treated samples did not feel as slippery as the finished product. Before drawing any conclusion, it is suggested to wait for the results of the quantitative testing at ConvaTec.

Conclusions

Successful deposition of PEG-like coatings using the most promising conditions from the first series of trials+one extra condition (#4), in which precursor mass feed was increased and the number of passes decreased. In all cases, high and persistent wettability of the treated surfaces was demonstrated.

Qualitative feel test revealed improved lubricity, but not yet close to the one of the current finished product.

Seven (7) straight tubes and eight (8) formed catheters were produced for each of the three tested conditions, 1, 3 and 4. Label "A" refers to the straight tubes, "B" to the formed catheters, in total, 45 samples were produced during the day, and have been shipped along with some untreated samples.

While this disclosure has been described with respect to at least one embodiment, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. A method of modifying a medical device, the method comprising:
functionalizing a surface of the medical device using cold plasma,
wherein:
functionalizing the surface of the medical device using cold plasma comprises contacting the surface with cold plasma to provide a plasma-treated surface and performing cold plasma treatment at a temperature between 15° C. and 40° C.,
contacting the surface with cold plasma comprises introducing a monomer to cold plasma to create monomer plasma and applying the monomer plasma to the surface to provide the plasma-treated surface,
the method further comprises mixing the monomer with a precursor gas stream consisting of nitrogen gas,
functionalizing the surface using cold plasma comprises functionalizing the plasma-treated surface with a polymer, and
the polymer or the monomer is a polyalkylene glycol having a reactive end group.

2. The method of claim 1, wherein functionalizing the plasma-treated surface with the polymer includes plasma polymerizing the monomer plasma onto the plasma-treated surface.

3. The method of claim 1, wherein:
contacting the surface with cold plasma comprises treating the surface with cold plasma to create reactive sites or polymerization initiation sites on the surface; and
functionalizing the plasma-treated surface with the polymer comprises reacting, simultaneously or subsequently, a polymer or a monomer with the plasma-treated surface to functionalize the surface with the polymer or the monomer.

4. A method of modifying a medical device, the method comprising:
functionalizing a surface of the medical device using cold plasma,
wherein:
functionalizing the surface of the medical device using cold plasma comprises contacting the surface with cold plasma to provide a plasma-treated surface and performing cold plasma treatment at a temperature between 15° C. and 40° C.,
contacting the surface with cold plasma comprises introducing a monomer to cold plasma to create monomer plasma and applying the monomer plasma to the surface to provide the plasma-treated surface,
the method further comprises mixing the monomer with a precursor gas stream consisting of nitrogen gas,
functionalizing the surface using cold plasma comprises functionalizing the plasma-treated surface with a polymer,
the polymer or the monomer is a polyalkylene glycol having a reactive end group, and
wherein the polymer or the monomer is selected from the group including an acrylate-functionalized polyalkylene glycol and an alkylacrylate polyalkylene glycol.

5. A method of modifying a medical device, the method comprising:
functionalizing a surface of the medical device using cold plasma,
wherein:
functionalizing the surface of the medical device using cold plasma comprises contacting the surface with cold plasma to provide a plasma-treated surface and performing cold plasma treatment at a temperature between 15° C. and 40° C.,
contacting the surface with cold plasma comprises introducing a monomer to cold plasma to create monomer plasma and applying the monomer plasma to the surface to provide the plasma-treated surface,
the method further comprises mixing the monomer with a precursor gas stream consisting of nitrogen gas,
functionalizing the surface using cold plasma comprises functionalizing the plasma-treated surface with a polymer,
the polymer or the monomer is a polyalkylene glycol having a reactive end group, wherein the polymer or the monomer is selected from the group including an acrylate-functionalized polyalkylene glycol and an alkylacrylate polyalkylene glycol, and wherein the polymer or the monomer is selected from the group including an acrylate- or methacrylate-functionalized polyethylene or polypropylene glycol.

6. The method of claim 1, further comprising creating a hydrophilic surface or a hydrophobic surface.

7. The method of claim 1, wherein functionalizing the surface of the medical device using cold plasma comprises performing cold plasma treatment at (i) a pressure of between 0.5 and 1500 mbar and (ii) a plasma power of between 1 W and 2000 W.

8. The method of claim 7, wherein functionalizing the surface of the medical device using cold plasma comprises performing cold plasma treatment at a plasma power of between 5 W and 100 W.

9. A method of modifying a medical device, the method comprising:

combining a monomer with a cold plasma;

creating a monomer plasma of the monomer; and graft polymerizing the monomer plasma onto a surface of the medical device, wherein combining the monomer with the cold plasma comprises combining a monomer having the following formula with the cold plasma:

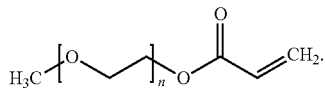

Formula I

10. The method of claim 9, further comprising mixing the monomer with a precursor fluid or plasma gas selected from the group including hydrogen, oxygen, nitrogen, air, ammonia, argon, helium, carbon dioxide, water, methane, ethane, propane, butane, or any mixture thereof.

11. The method of claim 9, wherein the monomer is a polyalkylene glycol having a reactive end group.

12. The method of claim 11, wherein the monomer is selected from the group including an acrylate-functionalized polyalkylene glycol and an alkylacrylate polyalkylene glycol.

13. The method of claim 9, further comprising creating a hydrophilic surface or a hydrophobic surface.

14. A method of modifying a medical device, the method comprising:

combining a monomer with a cold plasma;

creating a monomer plasma of the monomer; and graft polymerizing the monomer plasma onto a surface of the medical device to create a hydrophilic surface or a hydrophobic surface, wherein graft polymerizing the monomer plasma onto the surface of the medical device comprises performing cold plasma treatment at a temperature between 15° C. and 40° C., wherein combining the monomer with the cold plasma comprises mixing the monomer with a precursor gas stream consisting of nitrogen gas, and wherein the monomer is a polyalkylene glycol having a reactive end group.

* * * * *